(12) United States Patent
Matsushita et al.

(10) Patent No.: US 10,376,474 B2
(45) Date of Patent: *Aug. 13, 2019

(54) FENTANYL-CONTAINING PATCH FOR EXTERNAL USE

(71) Applicant: TEIKOKU SEIYAKU CO., LTD., Kagawa (JP)

(72) Inventors: Kunihiko Matsushita, Kagawa (JP); Mamoru Naruse, Tokushima (JP); Kenichi Hattori, Tokushima (JP)

(73) Assignee: TEIKOKU SEIYAKU CO., LTD., Kagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/345,603

(22) Filed: Nov. 8, 2016

(65) Prior Publication Data

US 2017/0071872 A1    Mar. 16, 2017

Related U.S. Application Data

(63) Continuation of application No. 12/864,932, filed as application No. PCT/JP2009/051172 on Jan. 26, 2009, now Pat. No. 9,517,211.

(30) Foreign Application Priority Data

Jan. 28, 2008  (JP) .................. 2008-015875

(51) Int. Cl.
| | |
|---|---|
| A61K 9/70 | (2006.01) |
| A61K 31/4468 | (2006.01) |
| A61P 25/04 | (2006.01) |
| A61K 47/06 | (2006.01) |
| A61K 47/14 | (2017.01) |
| A61K 47/32 | (2006.01) |
| A61K 9/00 | (2006.01) |

(52) U.S. Cl.
CPC .......... *A61K 9/7076* (2013.01); *A61K 9/0014* (2013.01); *A61K 9/7023* (2013.01); *A61K 9/7053* (2013.01); *A61K 31/4468* (2013.01); *A61K 47/06* (2013.01); *A61K 47/14* (2013.01); *A61K 47/32* (2013.01)

(58) Field of Classification Search
None
See application file for complete search history.

(56) References Cited

U.S. PATENT DOCUMENTS

| | | |
|---|---|---|
| 4,588,580 A | 5/1986 | Gale et al. |
| 5,352,457 A | 10/1994 | Jenkins |
| 6,139,866 A | 10/2000 | Chono et al. |
| 7,504,114 B1 | 3/2009 | Kurita et al. |
| 2004/0234584 A1 | 11/2004 | Muller et al. |
| 2005/0129748 A1 | 6/2005 | Takada et al. |
| 2005/0220852 A1 | 10/2005 | Shirai et al. |
| 2006/0013865 A1 | 1/2006 | Ito et al. |
| 2006/0034900 A1 | 2/2006 | Saeki et al. |
| 2006/0078603 A1 | 4/2006 | Nguyen |
| 2007/0009588 A1 | 1/2007 | Ito et al. |
| 2008/0089926 A1 | 4/2008 | Ishima et al. |
| 2009/0239828 A1 | 9/2009 | Yamazaki et al. |
| 2009/0246263 A1 | 10/2009 | Honma et al. |
| 2009/0258061 A1 | 10/2009 | Hwang |

FOREIGN PATENT DOCUMENTS

| | | |
|---|---|---|
| JP | 59-181211 | 10/1984 |
| JP | 61-37725 | 2/1986 |
| JP | 10-45570 | 2/1998 |
| JP | 2000-44476 | 2/2000 |
| JP | 2004-043512 | 2/2004 |
| JP | 2004-513890 | 5/2004 |
| JP | 2004-524336 | 8/2004 |
| JP | 2005-501111 | 1/2005 |
| JP | 2005-350403 | 12/2005 |
| JP | 2006-76994 | 3/2006 |
| JP | 2008-273865 | 11/2008 |
| WO | 00/61120 | 10/2000 |
| WO | 02/26217 | 4/2002 |
| WO | 02/074286 | 9/2002 |
| WO | 03/070228 | 8/2003 |
| WO | 2004/024155 | 3/2004 |
| WO | 2004/035054 | 4/2004 |
| WO | 2004/112770 | 12/2004 |

(Continued)

OTHER PUBLICATIONS

International Search Report dated Mar. 10, 2009 in International (PCT) Application No. PCT/JP2009/051172.
English translation of the International Preliminary Report on Patentability dated Sep. 16, 2010 in corresponding International (PCT) Application No. PCT/JP2009/051172.
Santus, G.C., et al., J. Control. Release (1993), 25: pp. 1-20.
Extended European Search Report dated Apr. 9, 2014 in corresponding Application No. 09 70 6430.

(Continued)

*Primary Examiner* — Kevin S Orwig

(74) *Attorney, Agent, or Firm* — Wenderoth, Lind & Ponack, L.L.P.

(57) ABSTRACT

A patch for external use which has a laminate structure comprising a substrate and a pressure-sensitive adhesive layer which contains a styrene/isoprene/styrene block copolymer as the base and further contains a tackifier resin consisting of a rosin resin and at least one other tackifier resin, a softening agent consisting of polybutene and liquid paraffin, a fatty acid ester, and fentanyl, characterized in that the weight ratio of the rosin resin to fentanyl is 1 to 5, the weight ratio of the rosin resin to the whole tackifier resin is 0.1 to 0.6, and the tackifier resin accounts for 30 to 60 wt % of the whole pressure-sensitive adhesive layer. The patch is excellent in the permeation of fentanyl through the skin and in storage stability, and is weak in irritation to skin.

1 Claim, 1 Drawing Sheet

(56) References Cited

FOREIGN PATENT DOCUMENTS

| WO | 2006/064576 | 6/2006 |
|----|-------------|--------|
| WO | 2008/007554 | 1/2008 |
| WO | 2008/032678 | 3/2008 |

OTHER PUBLICATIONS

Office Action dated Aug. 13, 2013 in corresponding Japanese Application No. 2009-551507.
NittoDenko (BusinessWeek Mar. 29, 2004).

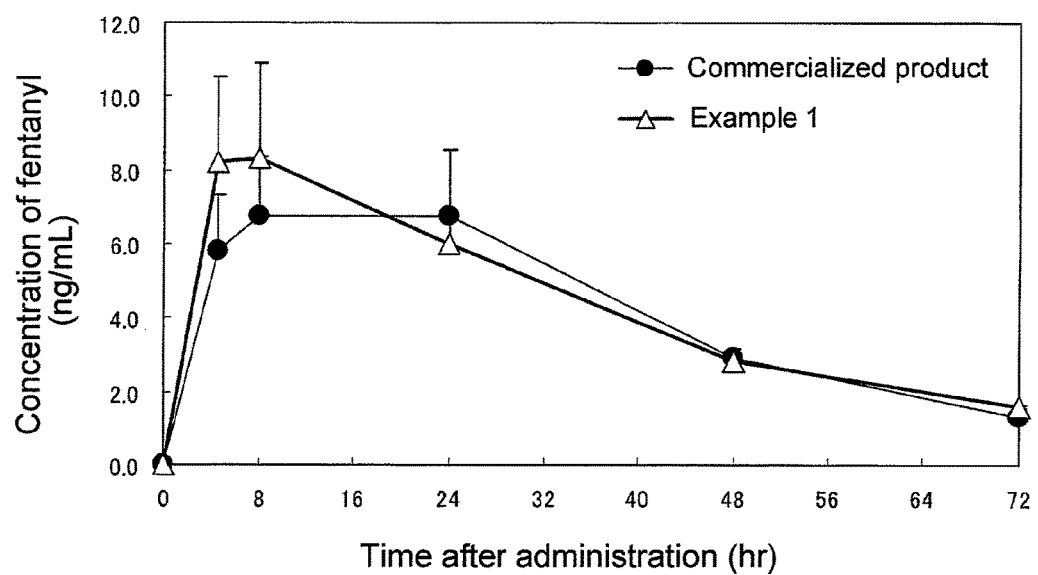

FENTANYL-CONTAINING PATCH FOR EXTERNAL USE

TECHNICAL FIELD

The present invention relates to a patch containing fentanyl for external use which is excellent in permeation of fentanyl through the skin and in storage stability, and weak in irritation to the skin.

BACKGROUND ART

Fentanyl and fentanyl citrate are synthetic narcotic analgesics which have been confirmed being about 200 times more potent in analgesic activity than morphine in animal experiments. Nowadays fentanyl-containing reservoir-type long-acting preparations of the percutaneous absorption type are commercially available for relieving cancer-caused pains and, with such preparations, the blood concentration of fentanyl can be maintained practically at effective levels for 24 to 72 hours.

However, such reservoir-type long-acting preparations of the percutaneous absorption type are disadvantageous in that the drug absorption after application thereof is fairly slow and the blood concentration arrives at an effective level only after 12 to 24 hours following the initial application, so that they cannot produce an immediate analgesic effect, in that because of their being reservoir-type preparations, they have the problem of fluid leakage, and in that they are very strong irritant to the lesion of application due to their containing ethanol.

Attempts have so far been made to produce matrix-type patches for percutaneous absorption as means for solving the above problems. For example, preparations for percutaneous absorption in which an acrylic adhesive is used as a main base are proposed in Patent Documents 1 and 2. However, the acrylic adhesive is generally inferior in drug-release, causing a problem: namely, a desired level of drug-release can be attained only by increasing the content of a main drug. The increase in the main drug content causes other problems, for example the problem of crystallization of the main drug during storage, and the problem of residual fentanyl in the preparation after application thereof. Preparations comprising polyisobutylene as the main base have also been disclosed in Patent Documents 3 and 4.

On the other hand, while fentanyl-containing patches in which a styrene-isoprene-styrene block copolymer (hereinafter abbreviated as "SIS") is used as a main base (SIS-based preparations) have also been disclosed in Patent Documents 5 and 6, there have not yet been developed any patches capable of simultaneously guaranteeing prolonged stable main drug-release on the occasion of use, long-term storage stability and safety to the skin during prolonged application thereto. It has been shown that N-methyl-2-pyrrolidone, for instance, used as an absorption enhancer in a SIS-based preparation has the effect of reducing the period of delay in percutaneous absorption owing to the absorption promoting action of N-methyl-2-pyrrolidone; since, however, N-methyl-2-pyrrolidone is volatile, there arises a problem: namely, N-methyl-2-pyrrolidone may evaporate during storage and/or application, possibly resulting in changes in drug-release (Patent Document 5). Furthermore, a patch for percutaneous administration of fentanyl or an analog thereof has been proposed in Patent Document 7. While this art, too, relates to a matrix type preparation which comprises a monolayer polymer phase, the preparation is characterized in that it is biologically equivalent to the commercially available fentanyl preparations mentioned above; therefore, as regards the time course of the blood concentration of fentanyl following administration, the preparation still has the drawback that it fails to produce an immediate analgesic effect, like the reservoir-type long-acting preparations of the percutaneous absorption type.

[Patent Document 1] Japanese Patent Publication (Tokuhyo) 2004-513890
[Patent Document 2] Japanese Patent Publication (Tokuhyo) 2005-501111
[Patent Document 3] WO 2004/024155 Gazette
[Patent Document 4] Japanese Patent Publication 2006-76994
[Patent Document 5] Japanese Patent Publication 2000-44476
[Patent Document 6] WO 2003/070228 Gazette
[Patent Document 7] Japanese Patent Publication (Tokuhyo) 2004-524336

DISCLOSURE OF INVENTION

Problem to be Solved by Invention

Accordingly, it is an object of the present invention to provide a patch containing fentanyl for external use which is excellent in the permeation of fentanyl through the skin and in storage stability and weak in irritation to the skin.

Means for Solving the Problem

The present inventors made intensive investigations in an attempt to solve the problems mentioned above and, as a result, found that the above-mentioned problems can be solved by adopting the means that the combination ratio between the active ingredient fentanyl and a rosin resin and the combination ratio between the rosin resin and all tackifier resins are optimized.

Namely, it was found that with respect to a patch for external use which is prepared by laminating on a backing a SIS-based pressure-sensitive adhesive layer containing a tackifier resin consisting of a rosin resin and at least one other tackifier resin; a softening agent consisting of polybutene and liquid paraffin; a fatty acid ester; and fentanyl as the active ingredient and which is excellent in the permeation of fentanyl through the skin, high in formulation stability and lowly irritant to the skin can be obtained when the weight ratio of the rosin resin to fentanyl is 1 to 5 and the weight ratio of the rosin resin to the whole tackifier resin component is 0.1 to 0.6, the patch which is excellent in permeation of fentanyl through the skin, high in formulation stability and weak in irritation to the skin can be obtained. The present invention has been completed based on such findings.

Thus, the present invention relates to a fentanyl-containing patch for external use which has a laminate structure comprising a substrate and a SIS-based pressure-sensitive adhesive layer, characterized in that the pressure-sensitive adhesive layer further comprises a tackifier component (preferably in an amount of 30 to 60% by weight) consisting of a rosin resin and at least one other tackifier resin, a softening agent (preferably in an amount of 5 to 40% by weight) consisting of polybutene and liquid paraffin, a fatty acid ester (preferably in an amount of 1 to 20% by weight), and 1 to 10% by weight of fentanyl, with the weight ratio of the rosin resin to fentanyl being 1 to 5 and the weight ratio of the rosin resin to the whole tackifier resin component being 0.1 to 0.6.

Effects of the Invention

As a result of employing such a characteristic constitution as mentioned above, the patch according to the present invention is excellent in the permeation of fentanyl through the skin, high in storage stability and lowly irritant to the skin. It is an effect of the present invention that such a patch can be provided.

Furthermore, when the tackifier resin combination comprises a rosin resin and a petroleum resin, the solubility of fentanyl in the preparation, the main drug-releasing characteristics and the adhesiveness to the skin are well balanced. Further, the skin permeability of fentanyl can be increased by adding a fatty acid ester, in particular isopropyl myristate, as an absorption enhancer to the pressure-sensitive adhesive layer. When liquid paraffin and polybutene are incorporated as softening agents in the pressure-sensitive adhesive layer, the adhesiveness to the skin and the main drug solubility in the preparation are well balanced and, in particular, it has been revealed that when the composition ratio of liquid paraffin to polybutene is within the range of 0.5:1 to 3:1, most pronounced effects can be obtained; thus, the main drug in the preparation can be prevented from crystallizing and, further, a patch lowly irritant to the skin can be obtained.

In addition, it has also been revealed that when the level of addition of the tackifier resins is not lower than 30% relative to the whole pressure-sensitive adhesive layer, the patch according to the present invention can be obtained with a higher level of adhesiveness to the skin.

BRIEF DESCRIPTION OF DRAWINGS

FIG. 1 The FIGURE shows results of plasma concentration assaying on rabbit carried out in Test Example 4.

BEST MODE FOR CARRYING OUT THE INVENTION

The combination ratio of the SIS used as the main base constituent in the pressure-sensitive adhesive layer according to the present invention to the whole pressure-sensitive adhesive layer is preferably 5 to 50% by weight, more preferably 10 to 30% by weight.

The tackifier resins to be incorporated in the pressure-sensitive adhesive layer according to the present invention, which when mixed with the SIS, provide with tackiness to the skin, include rosin resins as well as petroleum resins, polyterpene resins, phenol resins, terpene phenol resins, xylene resins, and the like. As the rosin resins, there may be mentioned rosin esters, hydrogenated rosins, glycerin rosin esters, hydrogenated rosin glycerol esters, rosin acids, polymerized rosins, and the like; hydrogenated rosin glycerol esters are particularly preferred, however.

Preferably used as tackifier resins other than rosin resins are petroleum resins, including aliphatic saturated hydrocarbon resins, alicyclic saturated hydrocarbon resins, aromatic hydrocarbon resins, and the like; among them, alicyclic saturated hydrocarbon resins are more preferred.

The tackifier resins are used in an amount of 30 to 60% by weight to the weight of the whole pressure-sensitive adhesive layer. At levels lower than 30% by weight, tack characteristics unfavorably become poor for a patch, while at levels higher than 60% by weight, the tackiness unfavorably becomes so strong that physical skin irritation occurs on the occasion of peeling off the preparation from the skin.

When the balance between the solubility of fentanyl in the preparation and the percutaneous permeability thereof is taken into consideration, it is effective to add the rosin resin in an amount (at a weight ratio) of 1 to 5 times, preferably 2 to 4 times the amount of fentanyl. At rosin resin levels higher than 5 times the amount of fentanyl, the percutaneous permeability of the drug decreases and, at levels lower than 1 time, the solubility of the drug decreases and unfavorable influences are exerted on the physical characteristics of the preparation, for example crystallization of the main drug component.

The composition ratio (ratio by weight) of the rosin resin to the whole tackifier resin is preferably 0.1 to 0.6, more preferably 0.2 to 0.4. At rosin resin addition levels higher than 0.6 times the amount of the whole tackifier resin component, the percutaneous permeability of the drug decreases and, at levels lower than 0.1 times, the solubility of the drug decreases and unfavorable influences are exerted on the physical characteristics of the preparation, for example crystallization of the main drug component.

The fatty acid ester, when incorporated in the pressure-sensitive adhesive layer according to the present invention, serves as an absorption enhancer, and includes, but is not limited to, isopropyl myristate, diisopropyl adipate, diethyl sebacate, and the like; among them, isopropyl myristate is particularly preferred. The level of addition thereof in the pressure-sensitive adhesive layer is preferably 1 to 20% by weight, more preferably 2 to 10% by weight. When the fatty acid ester level is not higher than 1% by weight, the percutaneous drug permeation becomes insufficient while, at levels not lower than 20% by weight, the cohesive force of the pressure-sensitive adhesive layer decreases, unfavorably causing the problem of the base remaining on the skin.

The softening agent consisting of liquid paraffin and polybutene is incorporated in the pressure-sensitive adhesive layer according to the present invention to soften the pressure-sensitive adhesive and thereby improve the adaptability to the skin and, further, adjust the tackiness and reduce the physical skin irritation and, further, in consideration of the solubility of fentanyl and the effects on the physical characteristics of the preparation; the level of addition thereof is preferably 5 to 40% by weight, more preferably 10 to 30% by weight. At levels lower than 5% by weight, the adaptability to the skin becomes poor and the preparation easily peels off and, at levels higher than 40% by weight, the cohesive force of the pressure-sensitive adhesive decreases and adhesive deposits are unfavorably allowed to remain at the site of application. As for the solubility of fentanyl in liquid paraffin and polybutene, the solubility is higher in polybutene and the solubility of the main drug in the preparation can also be adjusted by the level of addition thereof. The liquid paraffin:polybutene mixing ratio is preferably 0.5:1 to 3:1, more preferably 1:1 to 2:1. When the proportion of liquid paraffin is higher than 3:1, the solubility of fentanyl in the preparation decreases and such an unfavorable influence as crystallization of the main drug is produced and, further, the adhesiveness of the preparation to the skin decreases. When the ratio is lower than 0.5:1, the tackiness becomes excessively strong and the skin irritation becomes strong.

As a base of the adhesive layer other than the SIS, one which is generally used in preparing patch pressure-sensitive adhesive layer is appropriately selected and added according to need for adjusting the adhesiveness and stability of the base. Specifically, water-absorbing macromolecules such as polyvinylpyrrolidone and polyvinylpyrrolidone/vinyl acetate copolymers, inorganic fillers such as titanium dioxide and silica species, dibutylhydroxytoluene (BHT) and the like may be added each at an appropriate level.

Fentanyl is incorporated in the pressure-sensitive adhesive layer according to the present invention preferably in an amount of 0.1 to 10% by weight, more preferably 1 to 8% by weight, most preferably 3 to 8% by weight.

The thickness of the pressure-sensitive adhesive layer according to the present invention is not particularly restricted; however, when the layer is too thin, the adhesive force decreases and, when it is too thick, the amount of the drug remaining unutilized in the preparation increases, the cost increases and the preparation becomes easily peelable upon rubbing against clothing; therefore, the thickness in question is desirably 20 to 100 µm.

Generally, it has been revealed that the flexibility and stretchability of a backing in the patch influence the adaptability to the skin and greatly contribute to improved percutaneous drug absorption. Therefore, the backing having high flexibility and stretchability is used in the patch according to the present invention as well and, as such backing, there may be mentioned a low-density polymer film, a nonwoven fabric, a woven fabric, and the like; from the viewpoints of general versatility and economy, among others, a polyethylene terephthalate film is desirable. Thickness of the film is desirably 0.1 to 100 µm. When the thickness is in excess of 100 µm, the patch can no longer adapt to or follow the unevenness and/or motion of the skin due to the stiffness of the polyethylene terephthalate film, with the result that the percutaneous absorption of the drug decreases.

The patch according to the present invention has a release liner on the pressure-sensitive adhesive layer. As the release liner, used is polyethylene terephthalate, polypropylene or paper, for instance. If necessary, the release liner is silicone-treated for optimizing the release force.

The patch according to the present invention can be prepared, for example, in the following manner.

The base, including the tackifier, is dissolved in an organic solvent, for example toluene, and then agitated and mixed with other components dissolved in an appropriate organic solvent. The obtained solution is applied onto a silicone-treated release liner, followed by 10 minutes of drying at 90° C. to form a pressure-sensitive adhesive layer with a thickness of 20 to 100 µm. The obtained pressure-sensitive layer is laminated with a polyethylene terephthalate substrate, followed by cutting to an appropriate size and shape, whereby the percutaneous absorption preparation according to the present invention can be obtained.

EXAMPLES

The following examples illustrate the present invention more specifically. They, however, by no means limit the scope of the present invention. In the examples, "part(s)" means "part(s) by weight", unless otherwise specified.

Examples 1 to 7

According to the formulations given in Table 1, respective patches for external use were produced. The rosin resin/fentanyl ratio (ratio by weight) and the rosin resin/total tackifier resin ratio (ratio by weight) are also shown in the table.

TABLE 1

| Composition | Ex. 1 | Ex. 2 | Ex. 3 | Ex. 4 | Ex. 5 | Ex. 6 | Ex. 7 |
|---|---|---|---|---|---|---|---|
| Styrene-isoprene-styrene block copolymer | 16 | 16 | 16 | 16 | 16 | 16 | 16 |
| Hydrogenated rosin glycerol ester | 15 | 5 | 9 | 24 | 10 | 15 | 15 |
| Alicyclic saturated hydrocarbon resin | 35 | 45 | 41 | 26 | 40 | 35 | 35 |
| Polybutene | 10 | 10 | 10 | 10 | 10 | 14 | 6 |
| Liquid paraffin | 11 | 15 | 11 | 11 | 15 | 7 | 15 |
| BHT | 2 | 2 | 2 | 2 | 2 | 2 | 2 |
| Isopropyl myristate | 5 | 5 | 5 | 5 | 5 | 5 | 5 |
| Fentanyl | 6 | 2 | 6 | 6 | 2 | 6 | 6 |
| Rosin resin/Fentanyl (ratio by weight) | 2.5 | 2.5 | 1.5 | 4.0 | 5.0 | 2.5 | 2.5 |
| Rosin resin/Whole tackifier resin (ratio by weight) | 0.30 | 0.10 | 0.18 | 0.48 | 0.20 | 0.30 | 0.30 |

Reference Examples 1-5

According to the formulations given in Table 2, respective patches for external use were produced. The rosin resin/fentanyl ratio (ratio by weight) and the rosin resin/total tackifier resin ratio (ratio by weight) are also shown in the table.

TABLE 2

| Composition | Ref. Ex. 1 | Ref. Ex. 2 | Ref. Ex. 3 | Ref. Ex. 4 | Ref. Ex. 5 |
|---|---|---|---|---|---|
| Styrene-isoprene-styrene block copolymer | 16 | 20 | 16 | 16 | 16 |
| Hydrogenated rosin glycerol ester | 5 | 4 | 12 | 15 | 15 |
| Alicyclic saturated hydrocarbon resin | 20 | 3 | 11 | 35 | 35 |
| Polybutene | 10 | 10 | 10 | 1 | 20 |
| Liquid paraffin | 40 | 54 | 38 | 20 | 1 |
| BHT | 2 | 2 | 2 | 2 | 2 |
| Isopropyl myristate | 5 | 5 | 5 | 5 | 5 |
| Fentanyl | 2 | 2 | 6 | 6 | 6 |
| Rosin resin/Fentanyl (ratio by weight) | 2.5 | 2.0 | 2.0 | 2.5 | 2.5 |
| Rosin resin/Whole tackifier resin (ratio by weight) | 0.20 | 0.57 | 0.52 | 0.30 | 0.30 |

Comparative Examples 1-9

According to the formulations given in Table 3-1 and Table 3-2, patches for external use of Comparative Examples 1 to 6 were prepared according to the production process mentioned above. In Comparative Example 7, a patch was produced referring to Example 1 in WO 2004/024155. In Comparative Example 8, a patch was produced referring to Test Example No. 6 in Japanese Patent Publication 2006-76994. In Comparative Example 9, any patch could not be produced due to lack of cohesive force.

TABLE 3-1

| Composition | Comp. Ex. 1 | Comp. Ex. 2 | Comp. Ex. 3 | Comp. Ex. 4 | Comp. Ex. 5 |
|---|---|---|---|---|---|
| Styrene-isoprene-styrene block copolymer | 16 | 20 | 16 | 16 | 16 |

TABLE 3-1-continued

| Composition | Comp. Ex. 1 | Comp. Ex. 2 | Comp. Ex. 3 | Comp. Ex. 4 | Comp. Ex. 5 |
|---|---|---|---|---|---|
| Hydrogenated rosin glycerol ester | 3 | 8 | 6 | 35 | 3 |
| Alicyclic saturated hydrocarbon resin | 47 | 3 | 44 | 15 | 47 |
| Polybutene | 10 | 10 | 10 | 10 | 10 |
| Liquid paraffin | 11 | 42 | 16 | 11 | 16.5 |
| BHT | 2 | 2 | 2 | 2 | 2 |
| Isopropyl myristate | 5 | 5 | 5 | 5 | 5 |
| Fentanyl | 6 | 10 | 1 | 6 | 0.5 |
| Rosin resin/Fentanyl (ratio by weight) | 0.5 | 0.8 | 6.0 | 5.8 | 6.0 |
| Rosin resin/Whole tackifier resin (ratio by weight) | 0.06 | 0.73 | 0.12 | 0.7 | 0.06 |

TABLE 3-2

| Composition | Comp. Ex. 6 | Comp. Ex. 7 | Comp. Ex. 8 | Comp. Ex. 9 |
|---|---|---|---|---|
| Styrene-isoprene-styrene block copolymer | 16 | 8 | | 3 |
| Hydrogenated rosin glycerol ester | 15 | | | 15 |
| Alicyclic saturated hydrocarbon resin | 35 | 44.5 | 29.2 | 35 |
| Polybutene | | | | 10 |
| Polyisobutylene (low molecular weight) | 8 | | 37.2 | |
| Polyisobutylene (higher molecular weight) | 13 | 8 | 26.6 | |
| Liquid paraffin | | 36.7 | | 24 |
| BHT | 2 | | | 2 |
| Isopropyl myristate | 5 | | 5 | 5 |
| Fentanyl | 6 | 2 | 2 | 6 |
| Aluminum silicate | | | 0.8 | |

Test Example 1: Rat Skin Penetration Test In Vitro

The patches of Examples 1, 3, 4, 5, 6 and 7, Reference Examples 1 to 5 and Comparative Examples 3 to 8 were subjected to rat skin penetration test in vitro for fentanyl-release.

A skin segment excised from the rat abdomen of removal of hairs was set on a Franz cell, the cell was filled with phosphate-buffered saline, and warm water at 37° C. was circulated through the water jacket. A circular sample (16 mm in diameter) was punched out from each preparation and applied to the rat excised skin, the receptor liquid was sampled with time, the amount of fentanyl that had permeated was determined by liquid chromatography, and permeation rate (4-12 hr) was calculated. The results thus obtained are shown in Table 4-1, Table 4-2 and Table 4-3.

TABLE 4-1

| Sample | Ex. 1 | Ex. 3 | Ex. 4 | Ex. 5 | Ex. 6 | Ex. 7 |
|---|---|---|---|---|---|---|
| Fentanyl concentration (%) | 6 | 6 | 6 | 2 | 6 | 6 |
| Rate of release ($\mu g/cm^2/hr$) | 8.7 | 8.3 | 9.3 | 4.3 | 9.0 | 11.7 |

TABLE 4-2

| Sample | Ref. Ex. 1 | Ref. Ex. 2 | Ref. Ex. 3 | Ref. Ex. 4 | Ref. Ex. 5 |
|---|---|---|---|---|---|
| Fentanyl concentration (%) | 2 | 2 | 6 | 6 | 6 |
| Rate of release ($\mu g/cm^2/hr$) | 3.5 | 5.2 | 11.9 | 9.5 | 8.7 |

TABLE 4-3

| Sample | Comp. Ex. 3 | Comp. Ex. 4 | Comp. Ex. 5 | Comp. Ex. 6 | Comp. Ex. 7 | Comp. Ex. 8 |
|---|---|---|---|---|---|---|
| Fentanyl concentration (%) | 1 | 6 | 0.5 | 6 | 2 | 2 |
| Rate of release ($\mu g/cm^2/hr$) | 1.7 | 4.8 | 0.5 | 7.1 | 2.6 | 2.6 |

Test Example 2: Stability Test

The preparations of Examples 1, 2, 3 and 4 and Comparative Example 1 to 8 after 3 months of storage at room temperature were subjected to appearance observation by visual inspection; the results are shown in Table 5. The preparations showing precipitation of crystal were evaluated as "X" and the preparations showing no precipitation of crystal as "O".

TABLE 5

| Sample | Ex. 1 | Ex. 2 | Ex. 3 | Ex. 4 | | | | |
|---|---|---|---|---|---|---|---|---|
| Observation result | ○ | ○ | ○ | ○ | | | | |
| Sample | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 |
| Observation result | X | X | ○ | ○ | ○ | X | ○ | X |

Test Example 3: Adhesiveness Test

The preparations of Examples 1, 2, 3, 4, 5, 6 and 7, Reference Examples 1 to 5 and Comparative Examples 1 to 8 were each subjected to 180° peeling-off test using a tensile tester (Rheometer CR500DX, product of Sun Scientific Co., Ltd.) to evaluate the adhesiveness. The results thus obtained are shown in Table 6-1, Table 6-2 and Table 6-3.

TABLE 6-1

| Sample | Ex. 1 | Ex. 2 | Ex. 3 | Ex. 4 | Ex. 5 | Ex. 6 | Ex. 7 |
|---|---|---|---|---|---|---|---|
| Adhesiveness (g) | 305.3 | 256.8 | 522.1 | 420.0 | 346.3 | 688.3 | 220.1 |

TABLE 6-2

| Sample | Ref. Ex. 1 | Ref. Ex. 2 | Ref. Ex. 3 | Ref. Ex. 4 | Ref. Ex. 5 |
|---|---|---|---|---|---|
| Adhesiveness (g) | 8.0 | 4.7 | 17.9 | 144.8 | 1072.6 |

TABLE 6-3

| Sample | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 |
|---|---|---|---|---|---|---|---|---|
| Adhesiveness (g) | 349.9 | 7.5 | 225.3 | 395.8 | 276.6 | 481.1 | 207.6 | 831.2 |

Test Example 4: Rabbit Skin Primary Irritation Test

The patches of Examples 1, Example 2 and Comparative Example 8 were subjected to primary skin irritation testing on rabbits. Each patch was applied to the rabbit back of removal of hairs for 72 hours, and the irritation index (P.I.I.) was determined from the skin symptoms after 1 hour, 24 hours and 48 hours after peeling off. The evaluation criteria and the results are shown in Table 7-1 and Table 7-2, respectively.

TABLE 7-1

(Evaluation criteria)

| P.I.I | Stability class |
|---|---|
| P.I.I = 0 | Nonirritant |
| 0 < P.I.I < 2 | Weak irritant |
| 2 ≤ P.I.I < 5 | Medium irritant |
| 5 ≤ P.I.I | Strong irritant |

TABLE 7-2

(Result)

| Sample | Ex. 1 | Ex. 2 | Ex. 5 | Ex. 8 |
|---|---|---|---|---|
| Irritation index (P.I.I) | 1.8 | 1.6 | 2.2 | 3.0 |

Discussion (1) The results shown in Table 4-1 to Table 4-3 revealed that patches of Examples of the present invention are excellent in drug-release. In particular, it was revealed that those patches are excellent in drug-release as compared with the comparative example patches identical in drug concentration. The patches of Comparative Examples 3 to 5, 7 and 8 are considerably inferior in drug-releasing characteristics to the patches of the examples according to the present invention.
(2) The data shown in Table 5 and Table 7-2 revealed that the patches of the examples according to the present invention are superior in stability and safety. Crystal precipitation was observed in Comparative Examples 1, 2, 6 and 8.
(3) Further, the results shown in Table 4-1 to Table 7-1 revealed that the preparations of Comparative Examples 1, 2 and 6 have the problem of principal agent crystallization in the preparation, that the preparations of Comparative Examples 3, 4 and 5 show low levels of main drug-release, and that the preparation of Comparative Example 7 is low in main drug-release and also low in adhesiveness. It was further revealed that the preparation of Comparative Example 8 is low in main drug-release, allows crystallization of the main drug therein and is high in skin irritation although it is high in adhesiveness.

Test Example 5: Rabbit Plasma Concentration Measurement Test

The patch of Example 1 and a commercial product (reservoir-type patch containing fentanyl dissolved in ethanol) were subjected to rabbit plasma fentanyl concentration measurement (each dose being 5 mg). Each patch was applied to the depilated rabbit back for 72 hours, and blood samples were taken at timed intervals and subjected to liquid chromatography for plasma fentanyl concentration determination. The results thus obtained are shown in FIG. 1. It was revealed that the patch of the example according to the present invention is almost comparable to the commercial product in duration of action but shows a higher rate of initial increase in blood drug concentration.

INDUSTRIAL APPLICABILITY

The fentanyl-containing patch for external use according to the present invention is excellent in the permeation of fentanyl through the skin, high in formulation stability during storage and lowly irritant to the skin, and can be used for relieving pain in cancer patients, and the like.

The invention claimed is:
1. An external patch consisting essentially of an adhesive layer laminated on a support,
  wherein said adhesive layer consists essentially of:
    a styrene-isoprene-styrene block copolymer (SIS) base component;
    a tackifier component, wherein the tackifier component consists essentially of a hydrogenated rosin glycerol ester and an alicyclic saturated hydrocarbon resin;
    a softening component consisting of poly-butene and liquid paraffin;
    a fatty acid ester component, wherein the fatty acid ester component is isopropyl myristate;
    fentanyl; and
    optionally one or more ingredients selected from the group consisting of polyvinylpyrrolidone, polyvinylpyrrolidone/vinyl acetate copolymers, titanium dioxide, silica species, and dibutylhydroxytoluene,
  wherein:
    (1) the amount of said rosin resin is 1 to 5 times as much as the amount by weight of fentanyl,
    (2) the amount of said rosin resin is 0.1 to 0.6 times as much as the total amount by weight of the tackifier component,

(3) the amount of said tackifier component is 30 to 60% by weight based upon the total amount of components in the adhesive layer,
(4) the ratio by weight of liquid paraffin to poly-butene is 11:10 to 3:1, and
(5) the amount of said styrene-isoprene-styrene block copolymer (SIS) base component is 10 to 30% by weight, the amount of said softening component is 5 to 40% by weight, the amount of said fatty acid ester component is 1 to 20% by weight, and the amount of said fentanyl is 0.1 to 10% by weight, based upon the total amount of components in the adhesive layer.

* * * * *